US009821115B2

(12) United States Patent
Wozencroft

(10) Patent No.: US 9,821,115 B2
(45) Date of Patent: Nov. 21, 2017

(54) AUTOINJECTORS

(75) Inventor: Robert Wozencroft, Surrey (GB)

(73) Assignee: OWEN MUMFORD LIMITED, Oxford (GB)

( * ) Notice: Subject to any disclaimer, the term of this patent is extended or adjusted under 35 U.S.C. 154(b) by 1122 days.

(21) Appl. No.: 13/997,497

(22) PCT Filed: Dec. 22, 2011

(86) PCT No.: PCT/GB2011/052570
§ 371 (c)(1),
(2), (4) Date: Aug. 7, 2013

(87) PCT Pub. No.: WO2012/085588
PCT Pub. Date: Jun. 28, 2012

(65) Prior Publication Data
US 2013/0310746 A1 Nov. 21, 2013

Related U.S. Application Data

(60) Provisional application No. 61/426,079, filed on Dec. 22, 2010.

(30) Foreign Application Priority Data

Dec. 22, 2010 (GB) .................................. 1021771.9

(51) Int. Cl.
A61M 5/20 (2006.01)
A61M 5/315 (2006.01)
(Continued)

(52) U.S. Cl.
CPC ............ *A61M 5/20* (2013.01); *A61M 5/2033* (2013.01); *A61M 5/3157* (2013.01);
(Continued)

(58) Field of Classification Search
CPC .. A61M 5/20; A61M 5/2033; A61M 5/31533; A61M 2005/2073; A61M 5/326;
(Continued)

(56) References Cited

U.S. PATENT DOCUMENTS 4,031,893 A 6/1977 Kaplan et al.
5,360,409 A * 11/1994 Boyd, III ................ A61M 5/24
604/198

(Continued)

FOREIGN PATENT DOCUMENTS

EP 1 240 914 9/2002
GB 2 437 922 11/2007
(Continued)

OTHER PUBLICATIONS

JP Office Action, dated Sep. 15, 2015; Application No. 2013-545506.
(Continued)

Primary Examiner — Kevin C Sirmons
Assistant Examiner — Amber Stiles
(74) Attorney, Agent, or Firm — Young & Thompson

(57) ABSTRACT

An autoinjector includes a rear body assembly (10) connected to a front body assembly, wherein the rear body assembly (10) contains a drive mechanism (60 . . . ) and the front body assembly contains a syringe (13) or cartridge with a needle at its forward end, the front body assembly including a viewing window (22) through which at least part of the contents of the syringe (13) or cartridge are visible, a removable cap (14) fitted to the forward end of the front body assembly the rear body assembly and the removable cap having respective aligned cut-away regions together defining a frame for the viewing window. Also disclosed is a modular scheme which uses a common platform for the provision of a range of autoinjectors of different fill vol-
(Continued)

umes, with only the length of the plunger (60), and the axial extent of the cut out varying between different versions.

9 Claims, 12 Drawing Sheets

(51) Int. Cl.
*A61M 5/32* (2006.01)
*A61M 5/24* (2006.01)

(52) U.S. Cl.
CPC ....... *A61M 5/31533* (2013.01); *A61M 5/3204* (2013.01); *A61M 5/326* (2013.01); *A61M 2005/206* (2013.01); *A61M 2005/2073* (2013.01); *A61M 2005/2418* (2013.01); *A61M 2005/3247* (2013.01); *A61M 2205/581* (2013.01); *A61M 2207/00* (2013.01); *Y10T 29/49826* (2015.01); *Y10T 29/53* (2015.01)

(58) Field of Classification Search
CPC ........ A61M 2005/3247; A61M 5/3204; A61M 2207/00; A61M 2005/2418; A61M 2205/581; A61M 5/3157; Y10T 29/49826; Y10T 29/53
See application file for complete search history.

(56) References Cited

U.S. PATENT DOCUMENTS

| | | | |
|---|---|---|---|
| 7,955,303 B2 | 6/2011 | Burren et al. | |
| 2009/0192460 A1* | 7/2009 | Keller | A61M 5/1454 604/136 |

FOREIGN PATENT DOCUMENTS

| | | | |
|---|---|---|---|
| GB | 2465919 A | 6/2010 | |
| IL | WO 2008047372 A2 * | 4/2008 | ......... A61M 5/2033 |
| JP | 2009-507581 | 2/2009 | |
| WO | 2006/061170 | 6/2006 | |
| WO | 2010007395 A1 | 1/2010 | |
| WO | 2010076569 A2 | 7/2010 | |
| WO | 2010129583 A1 | 11/2010 | |
| WO | 2012/045350 | 4/2012 | |

OTHER PUBLICATIONS

GB Search Report, dated Mar. 4, 2011, from corresponding GB application.
International Search Report dated Jun. 29, 2012, corresponding to PCT/GB2011/052570.

\* cited by examiner

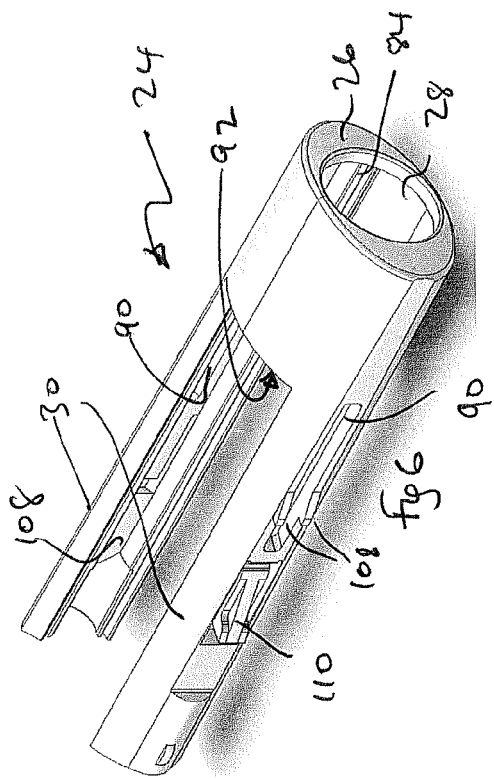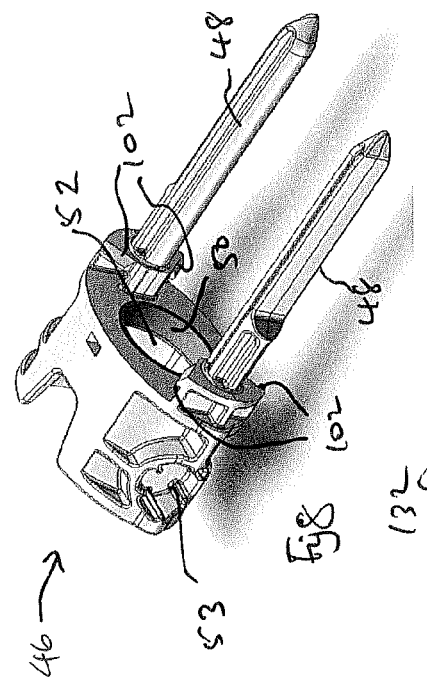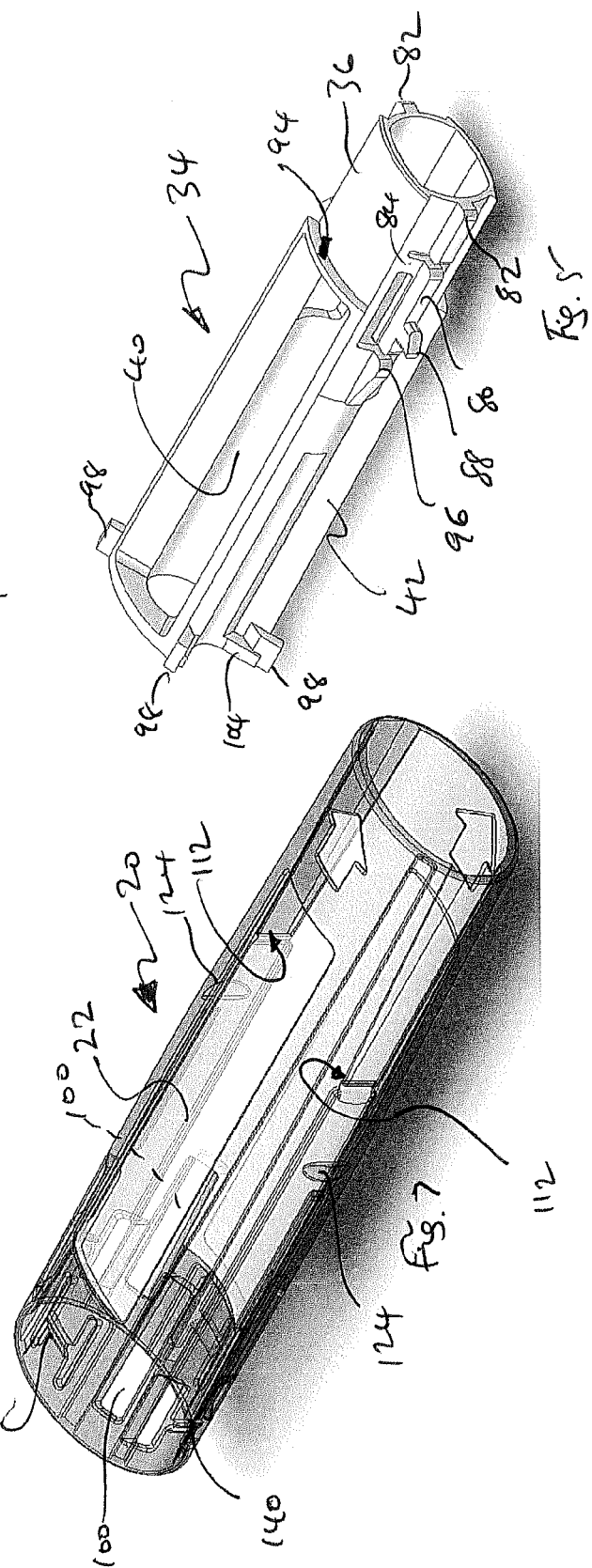

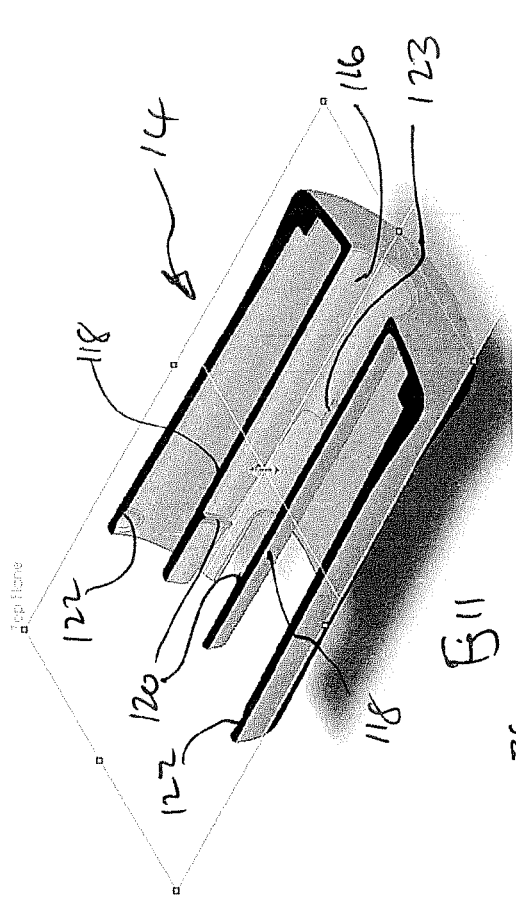
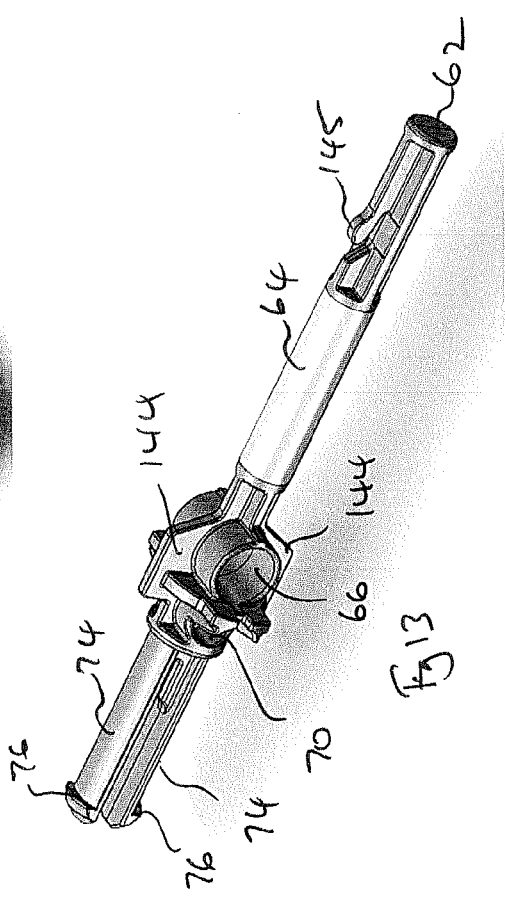
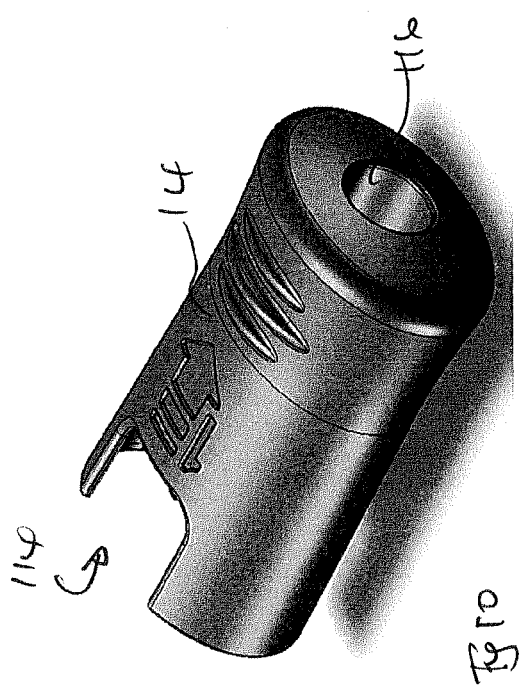
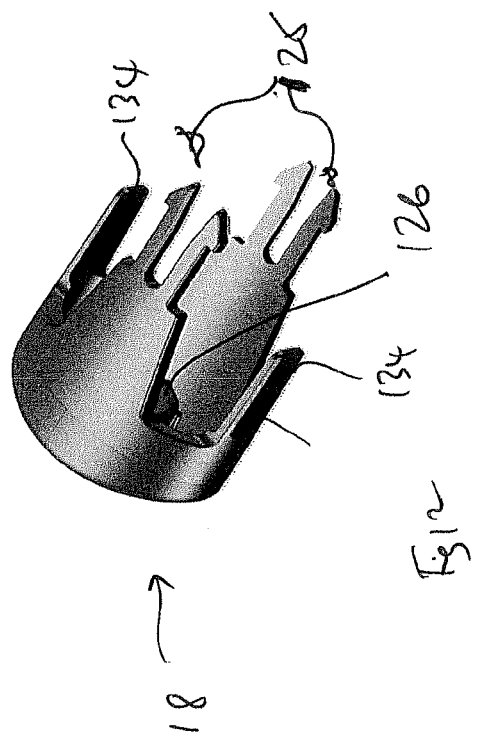

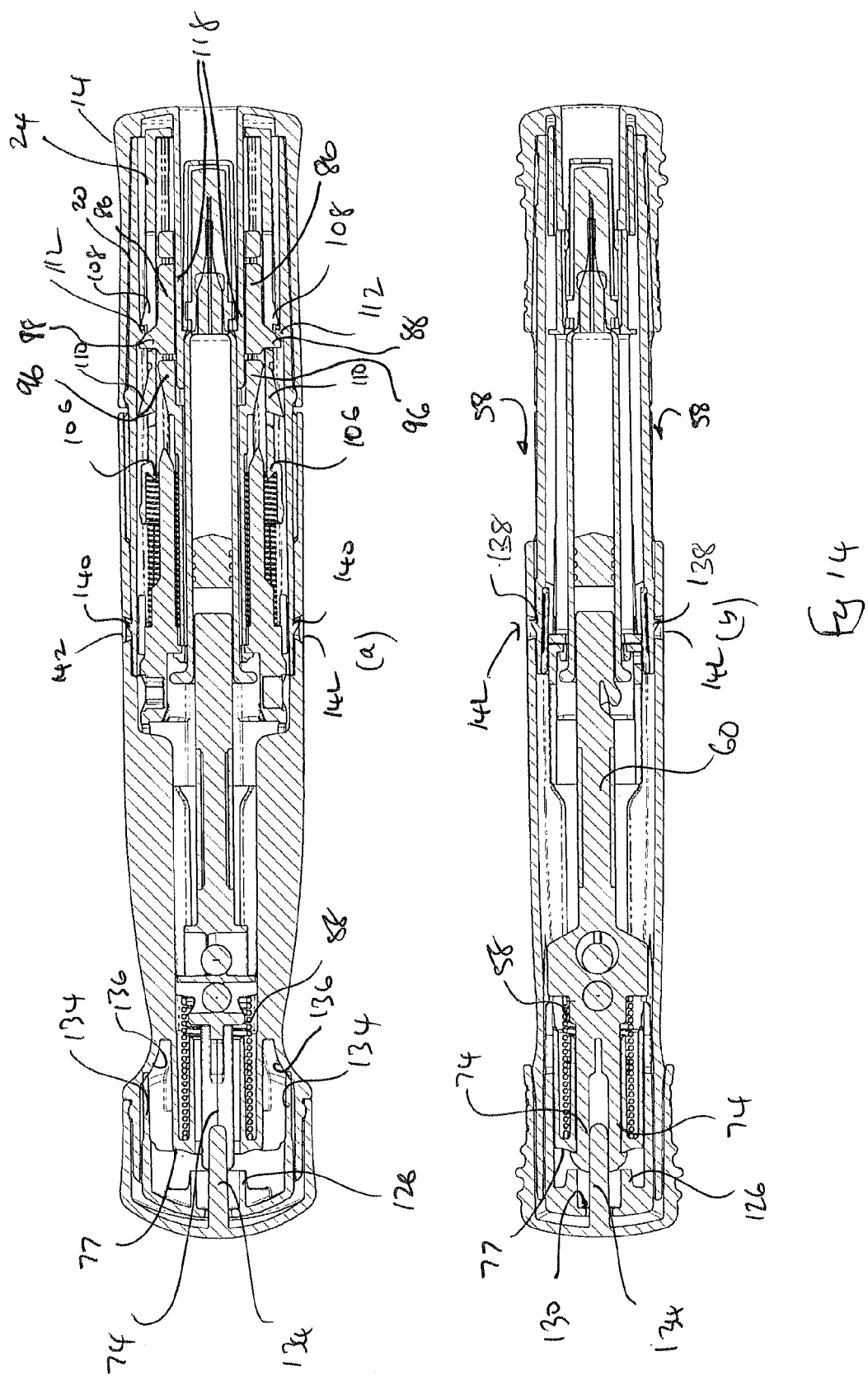

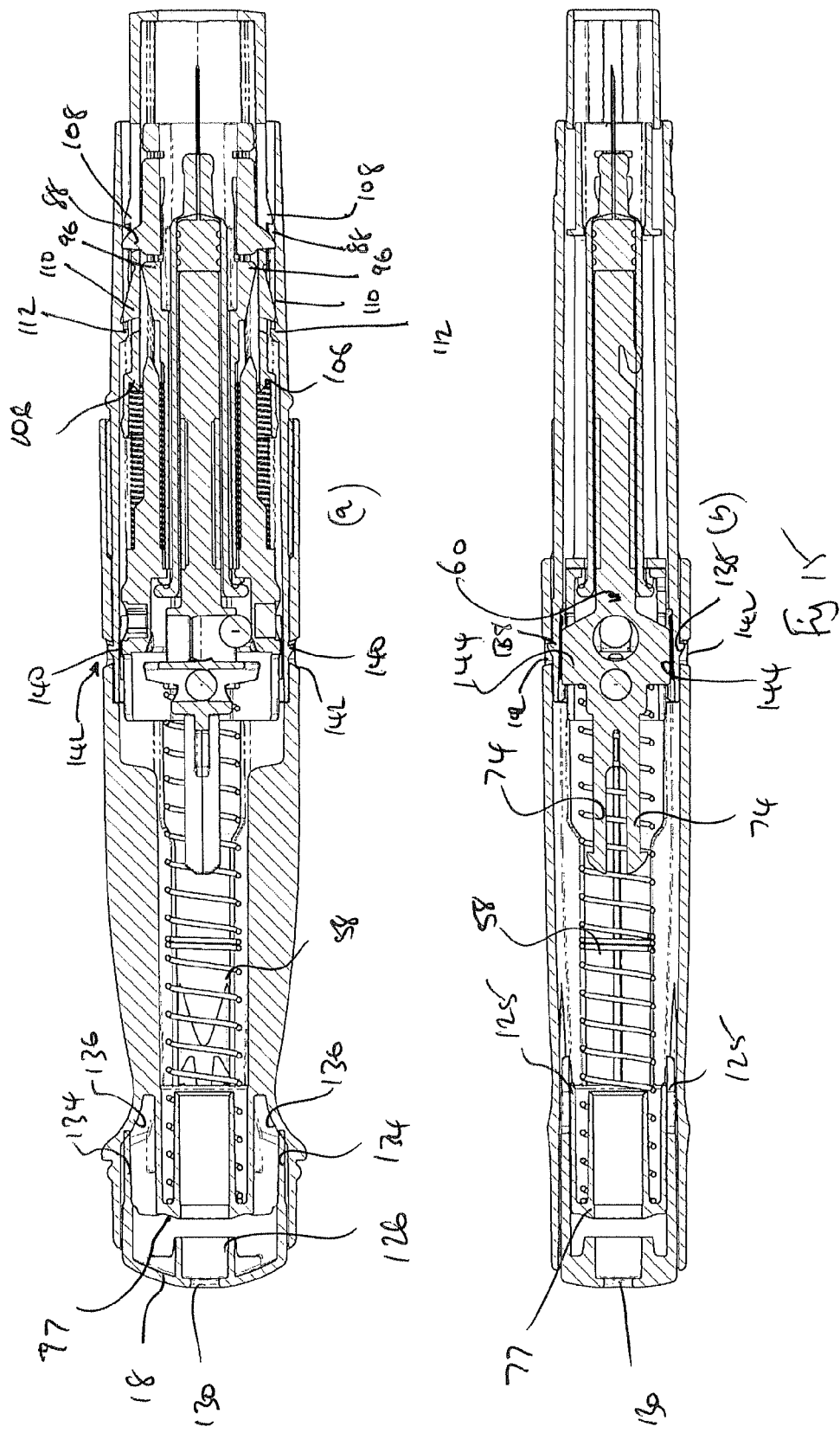

AUTOINJECTORS

This invention relates to autoinjectors.

Autoinjectors are commonly used to allow self-administration of medication particularly, but not exclusively, where regular ongoing treatment is required. In these circumstances the dose volume of the medication may vary according to the nature of the condition being treated, the phase of the treatment, the weight of the patient etc. For a number of reasons it is desirable that the appearance and operation of the device be similar and that components be shared between the devices However, in reality, the need to provide different dosage volumes can often require quite significant redesign of an autoinjector. This is expensive, both in terms of design and testing etc, but also in terms of manufacture and assembly.

Accordingly, we have designed an autoinjector which requires, in one particular example, design changes in just two components, with the remaining components being common to the autoinjectors for different dose volumes, whilst preserving all of the features and functionality of the original design.

Accordingly, in one aspect, this invention provides an autoinjector comprising a rear body assembly connected to a front body assembly, wherein said rear body assembly contains a drive mechanism and said front body assembly contains a syringe or cartridge with a needle at its forward end, the front body assembly including a viewing window through which at least part of the contents of the syringe or cartridge are visible, a removable cap fitted to the forward end of the forward body assembly, the rear body assembly and the removable cap having respective aligned cut-away regions together defining a frame for said viewing window. The frame is preferably rectangular to allow inspection of the contents of the syringe. Preferably substantially the entire length of the fill volume is visible; advantageously the longitudinal dimension of the frame is approximately equal to the length of the fill volume to within ±10%.

Preferably, the autoinjector is adapted to receive one of a series of syringes or cartridges of different dose volume, and the axial extent of at least one of said cut-away regions varies according to the fill volume.

In one embodiment, the extent of the cut-away region in the rear body assembly is one of a plurality of preset amounts. Likewise, in said drive mechanism the plunger may be selected from a group thereof of length dependent on the fill volume.

In another aspect, this invention provides a manufacturing system for manufacturing autoinjectors having a given number of different syringe fill volumes, the autoinjector comprising a rear body assembly containing a drive assembly including a plunger, a front body assembly containing a syringe or cartridge, the front body assembly and the rear body assemblies having respective housings with cut-away regions through which at least a major portion of the syringe or cartridge barrel and its contents are visible, the manufacturing system including providing a supply of rear body assemblies with cut-away regions of different axial extent and with different plungers, dependent on said fill volume, providing a supply of front assemblies of common design, and assembling said autoinjector, whereby a range of autoinjectors may be assembled for different fill volumes, in which apart from the fill volume only the axial extent of the cut out, and the plunger vary.

In yet another aspect, this invention provides a method of manufacturing one of a range of autoinjectors having syringes or cartridges with different preset fill volumes, which comprises:

providing a front body assembly, inserting a syringe or cartridge of given fill volume into said front body assembly, providing a rear body assembly which includes a rear body housing containing a drive plunger, the length of the drive plunger, the length of the drive plunger having been selected from a range of plungers of different length according to the fill volume of the syringe or cartridge, assembling said autoinjector by connecting together said front and rear body assemblies.

In this manner a range of autoinjectors of different fill volumes may be assembled using the same or similar assembly machinery, and the assembly line may rapidly switch from assembling autoinjectors of one fill volume to another.

Preferably the front body assembly is of common design for each of the range of autoinjectors. In many arrangements the front body assembly includes a removable cap fitted to the forward end thereof, and in such arrangements the rear body assembly and the removable cap may have respective aligned cut away regions that together define a viewing window through which the contents of the syringe or cartridge may be viewed in use. In this case the axial extent of the cut away region on the rear body assembly may be selected according to the fill volume of the syringe or cartridge Whilst the invention has been described above, it extends to any inventive combination or sub-combination of novel features set out above, or in thea following description or claims.

The invention may be performed in various ways and an embodiment thereof, with various modifications, will now be described by way of example only, reference being made to the accompanying drawings in which:

FIG. 5 is an enlarged view of the syringe carrier;

FIG. 6 is an enlarged view of the needle shroud;

FIG. 7 is an enlarged view of the front body housing;

FIG. 8 is an enlarged view of the spring guide;

FIG. 10 is an enlarged view of the front cap/needle shield remover;

FIG. 11 is a horizontal section view taken through the cap of FIG. on the major axis thereof;

FIG. 12 is an enlarged view of the trigger button;

FIG. 13 is an enlarged view of the plunger;

Figure 16:
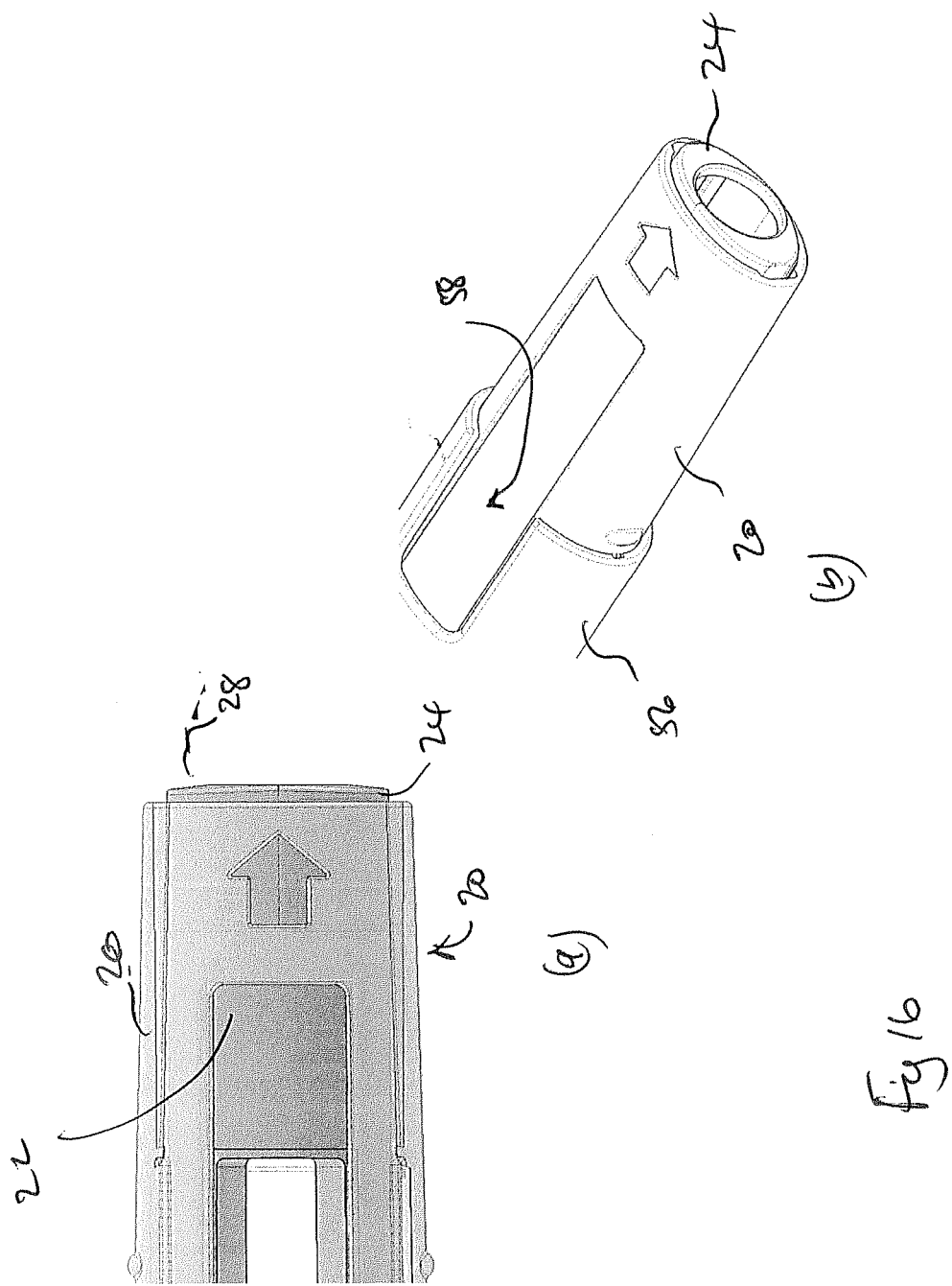
Figure 17:
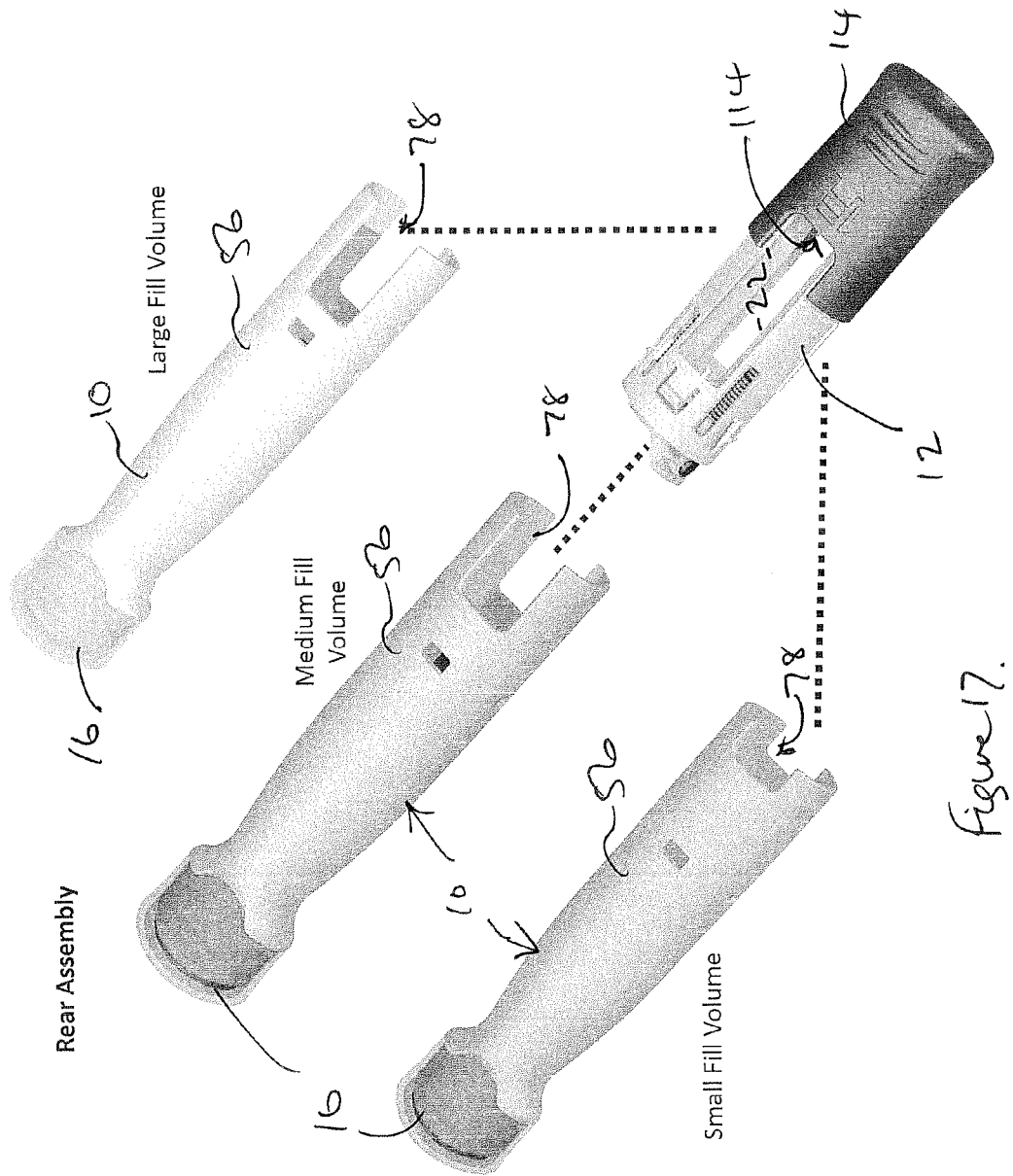
Figure 18:
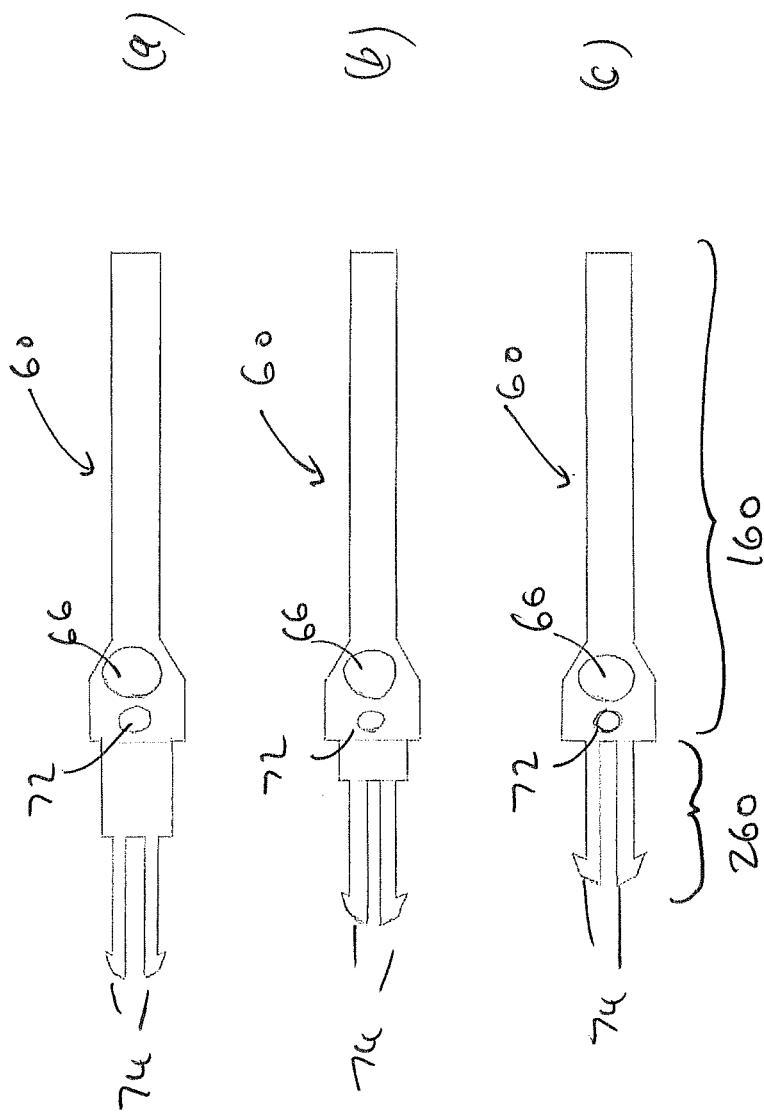

FIGS. 14(a) and (b) are transverse section views on the major and minor planes respectively of the autoinjector when in its pre-use condition;

FIGS. 15(a) and (b) are transverse section views on the major and minor planes respectively of the autoinjector after use;

FIGS. 16(a) and (b) are detail views on the front end of the device showing the forwardly dished skin-contact surface;

FIG. 17 is a schematic view illustrating the modular construction of a range of autoinjectors having small, medium and large fill volumes, and FIGS. 18(*a*), (*b*) and (*c*) are schematic views of the different plungers used for the small, medium and large fill volumes.

Figure 1:
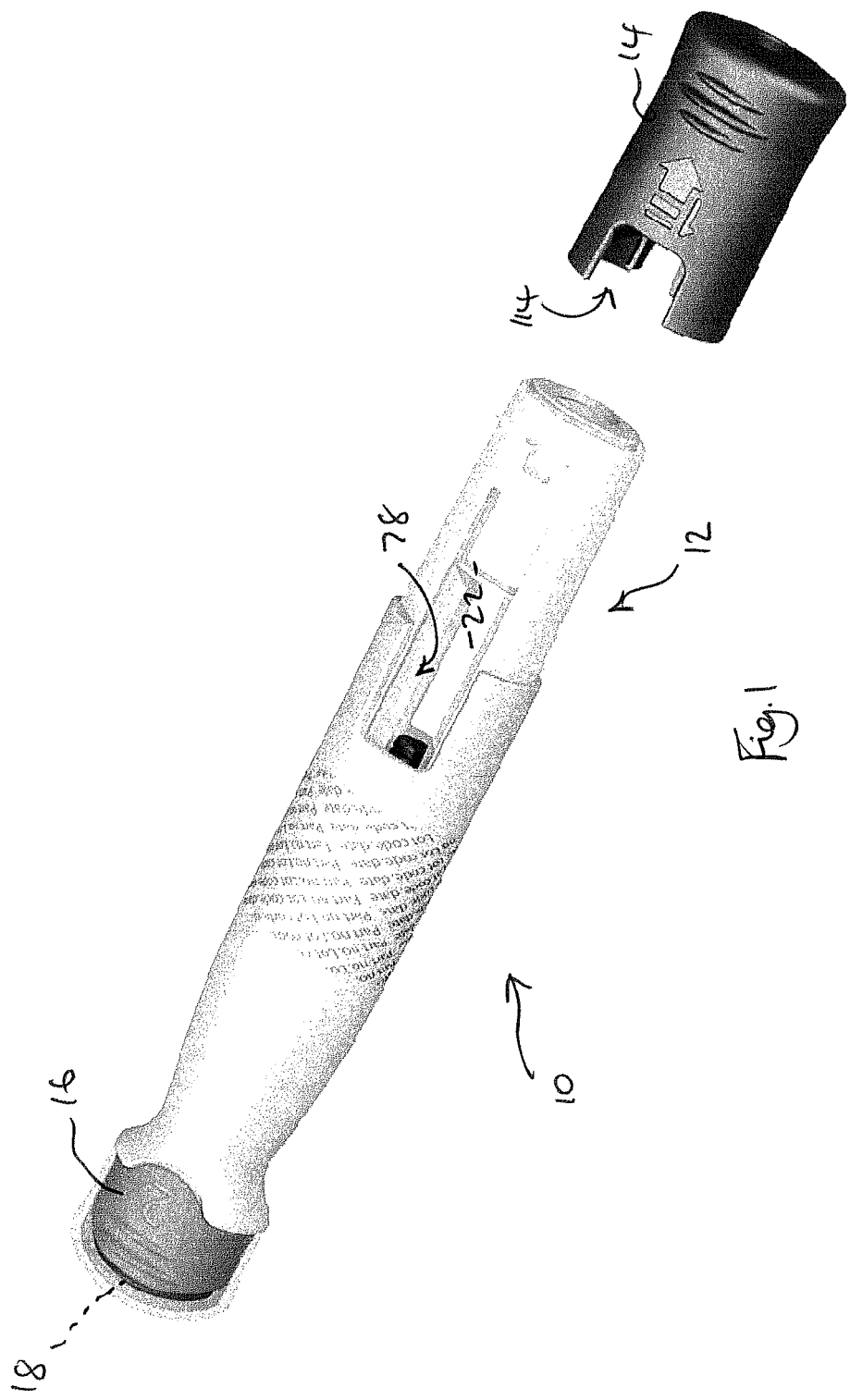
FIG. 1 is a perspective view of an autoinjector in accordance with an embodiment of this invention with the first, front cap removed prior to an injection, but before removal of the second, rear cap.
Figure 2:
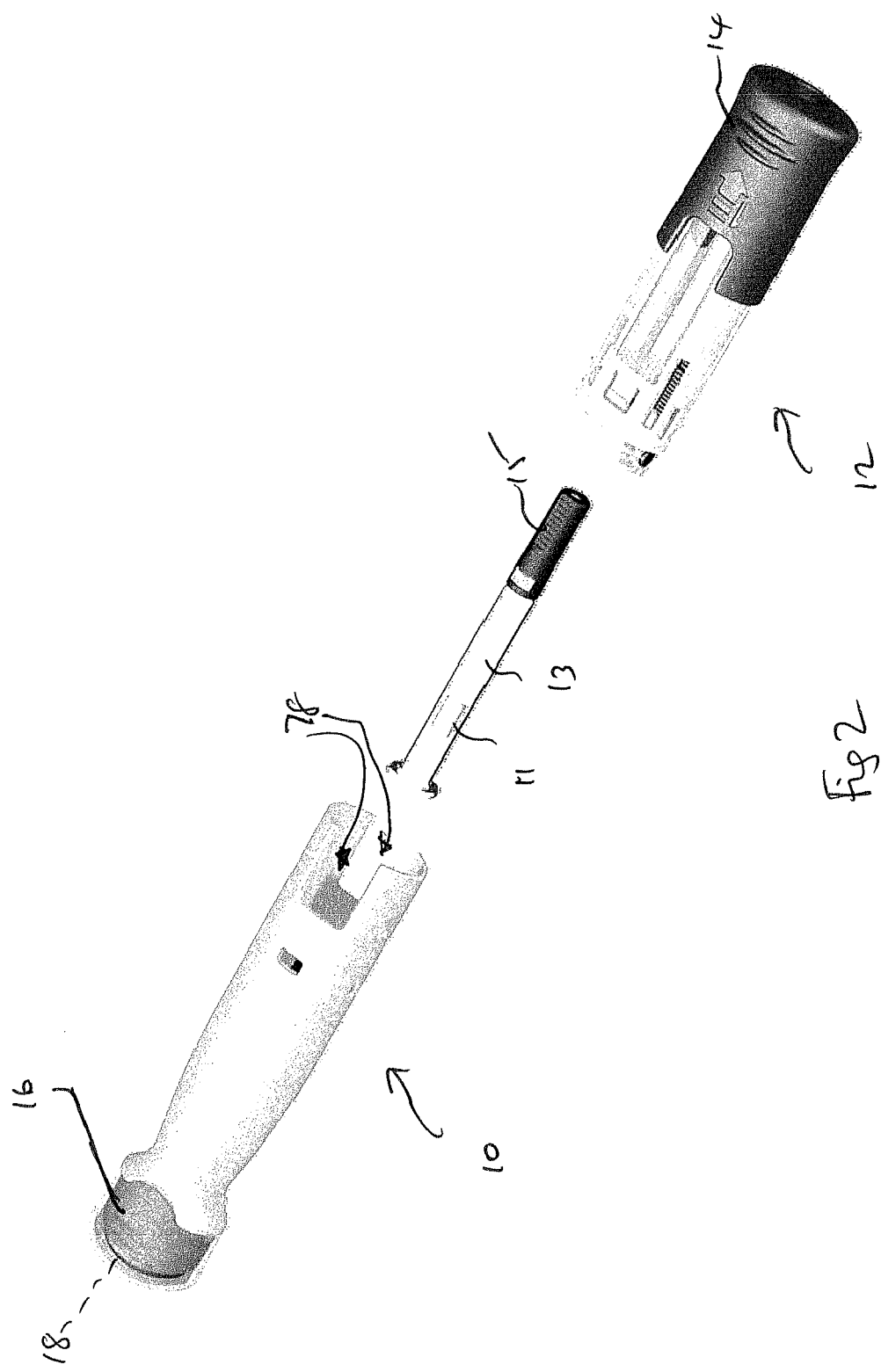
FIG. 2 is a view of the autoinjector with the rear assembly and front assembly separate prior to loading of a syringe in the forward assembly and being snap-fitted together.

The embodiment of autoinjector illustrated in the Figures and described below is designed automatically to inject a selected dose of medicament when offered up an injection site and fired. Referring initially to FIGS. 1 and 2, the autoinjector comprises a rear assembly 10 containing a drive mechanism and a front assembly 12 for receiving a syringe 13 with medicament. The front and rear assemblies are snap-fitted together during manufacture. On the front end of the device is a removable cap 14 that also serves as needle shield remover as to be described below. On the rear end of the rear assembly is a rear cap 16 which includes a safety pin which prevents premature firing of the drive mechanism, the rear cap also covering the firing button 18.

Figure 3:
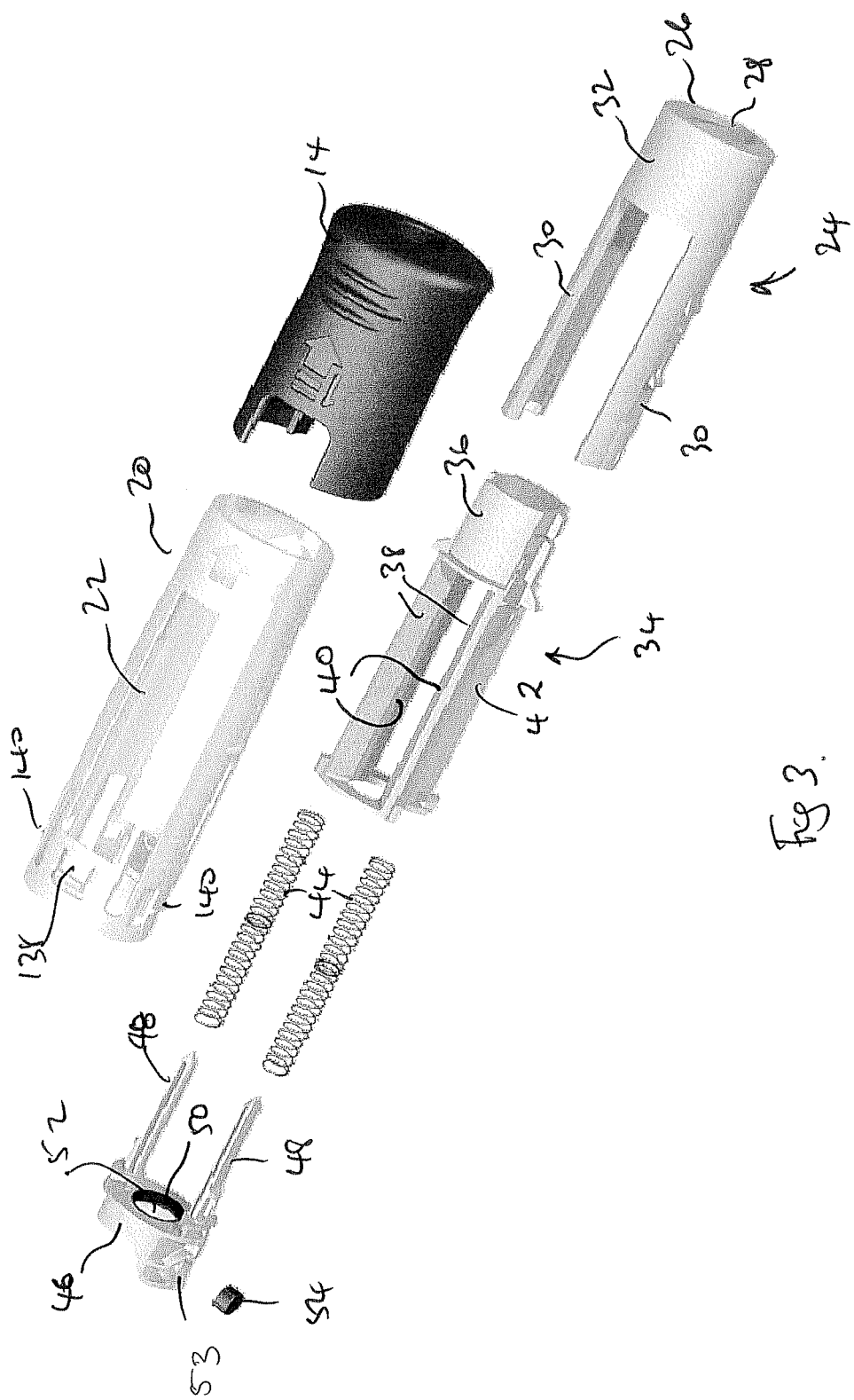
FIG. 3 is an exploded view of the front assembly.

Referring now to FIG. 3, the front assembly 12 comprises an outer body housing 20 of generally clear plastic material defining opposed integral viewing windows 22 through which the syringe can be viewed when the device has been assembled. The windows allow the whole of the dose volume of the syringe to be viewed. Apart from the clear plastic material of the windows 22, the body housing 20 may be opaque. Provision of a transparent window element, instead of the common arrangement of an open aperture or slot, has the advantage of preventing external access to the syringe. Also the provision of twin shroud springs spaced to either side of the longitudinal axis of the device means that the entire length of the dose volume is clearly visible without being obscured by any springs etc.

Slideably mounted within the housing 20 is a needle shroud 24 having a chamfered, conical and/or convexly curved domed front face 26 with a central aperture 28 therein to provide a forwardly dished configuration through which the needle of the syringe may project during the injection. The shroud 24 includes two rearwardly extending arms 30 of arcuate cross-section, extending back from a forward tubular section 32.

Slideably coupled to the needle shroud is a syringe carrier 34 having a forward tubular portion 36 capable of sliding telescopically inside the tubular portion 36 of the needle shroud 24. Extending rearwardly from the tubular portion 36 of the syringe carrier 34 are two arms 38 having opposed inner concave surfaces 40 for slideably receiving the barrel of a syringe and outer concave surfaces 42 for defining with convex inner arcuate surfaces on the arms 30 of the needle shroud 24, cylindrical containment spaces for a pair of shroud springs 44.

A spring guide 46 has two forwardly extending fingers 48 that pass down the centre of a respective spring 44. The spring guide 46 has an over-moulded liner 50 surrounding a circular aperture 52 through which a syringe is passed. The liner serves as a shock absorber for the syringe. The spring guide 46 is a snap fit with the rear end of the syringe carrier 34 as to be described below. The spring guide 46 has a rearwardly extending tubular portion in one side wall of which is a recess 53 for captively receiving a disc magnet 54.

Figure 4:
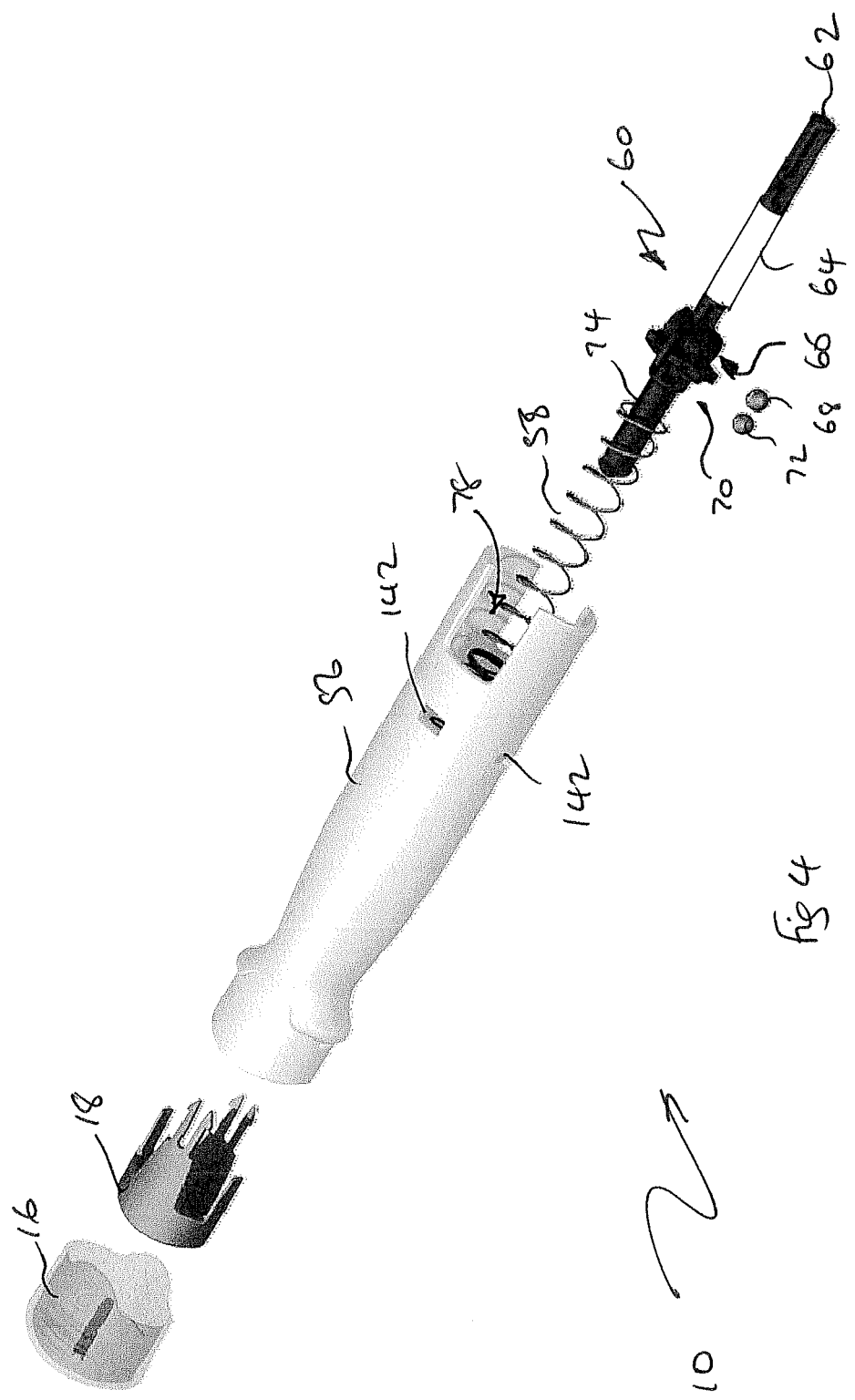
FIG. 4 is an exploded view of the rear assembly.
Figure 9:
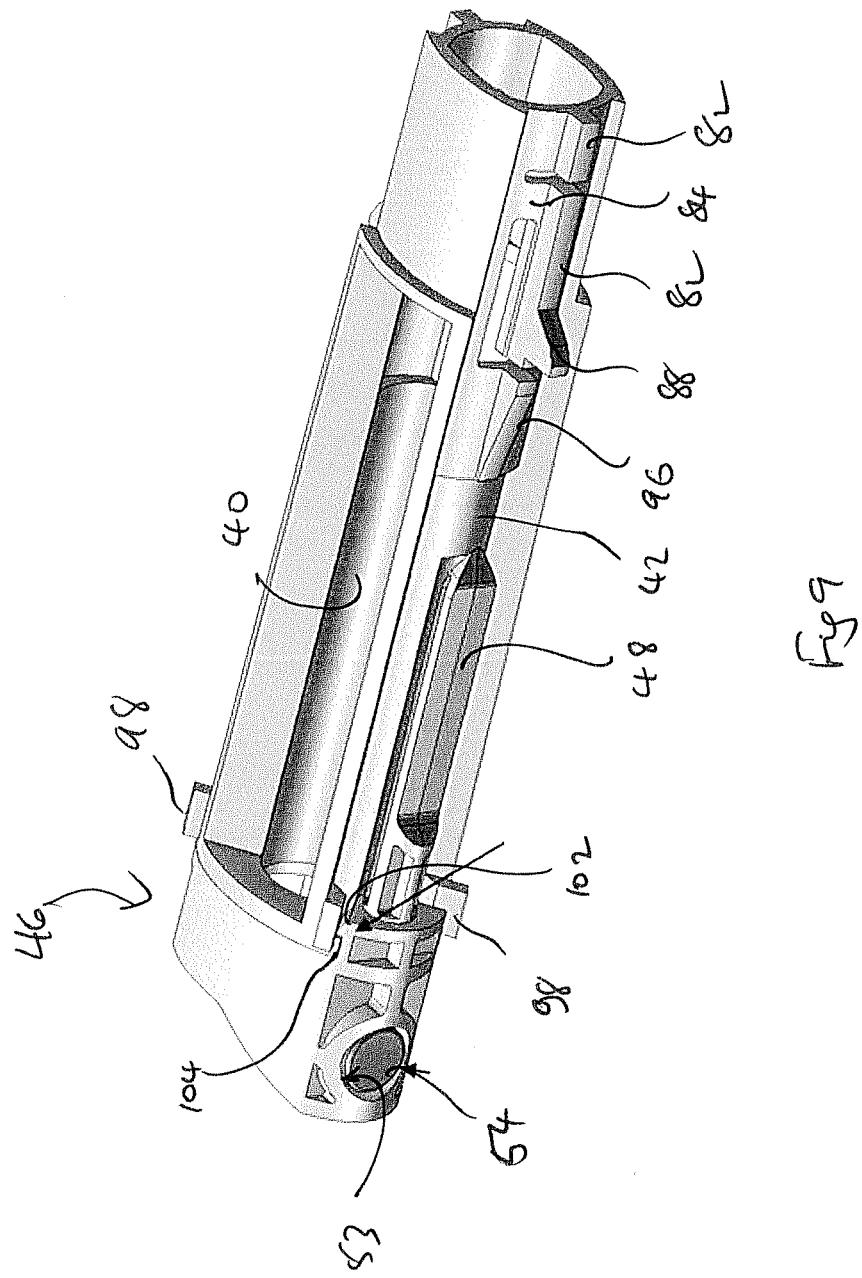
FIG. 9 is a view showing the spring guide and syringe carrier snap-fitted together.

Referring now to FIG. 4, the rear assembly comprises a rear body housing 56 in which is received the main drive spring 58 which acts on the rear end of a plunger 60. The plunger has a forward end 62 for engaging the piston 11 within a syringe and an over-moulded coloured indicator strip 64. To the rear of the indicator strip 64 is a transverse passage 66 in which is mounted for transverse movement a ball magnet 68. To the rear of the passage 66 is a provided a recess 70 which receives a ferro-magnetic keeper ball 72 which is fixedly disposed on the longitudinal axis of the plunger 60. The plunger 60 has two rearwardly extending split arrowhead limbs 74 with barbs 76 on the rear ends which seat around the edge of an annular catchment surface 77in the inside of the rear body housing 56 (see FIGS. 14 and 15) to latch the plunger in a cocked position, with the main spring 58 compressed.

Referring especially to FIGS. 17 and 18, the autoinjector is of modular construction designed to allow all except two components to be the same for autoinjectors with syringes of three different fill volumes. The shape and the size of the syringe itself is standard; only the fill volume and thus the fill length are different. The two components that vary are the rear body housing 10 and the plunger 60. The forward end of the rear body housing 52 contains opposed cut outs or slots 78 which are of variable length according to the fill volume contained in the syringe. The axial length of the slots 78 in the rear body housing 56 is proportional to the fill volume. As is evident by a comparison of FIGS. 18(*a*) to (*c*), a forward portion 160 of the plunger is the same length for all fill volumes but the length of a rear portion 260 varies inversely with the size of the fill length of the syringe. Also the indicator position moves by the same amount so that it arrives at the same place relative to the body at the end of the plunger stroke. The variation in length of the rear portion 260 of the plunger according to the fill volume of the syringe ensures that the magnet-containing passage 66 is located so that, at the end of its forward stroke, it reaches the same axial position with respect to the rear body housing 56 for each fill volume. In preferred embodiments, the plunger 60 and the axial length of the slots 78 are designed so that, for each of the plurality of fill volumes, the user will see prior to use in the viewing window 22 just that length of the syringe containing the dose, with the window being framed at the rear end by the slots 78. After the dose has been delivered, the indicator will be at the same forward position for each fill volume.

Thus the autoinjector makes use of a common front body assembly, with the rear body assembly being selected according to the fill volume of the syringe.

Referring now to FIGS. 5 to 9, the principal components of the front assembly will be described in more detail. The syringe carrier 34 has twin linear ribs provided to either side of the forward tubular portion 36. The ribs run in respective channels 84 on the inside of the tubular portion 32 of the needle shroud. Immediately behind each rib 82 is a live hinge 85 from which extends back a spring finger 86 with a barb 88 with a rearwardly inclined forward surface. When the syringe carrier is assembled telescopically into the needle shroud 24, the barbs 88 project through slots 90 in the shroud 24 (see FIG. 6) to limit forward movement of the shroud 24 relative to the syringe carrier 34 when the rear ends of the slots 90 contact the barbs 88. Rearward movement of the shroud 24 relative to the syringe cap is limited by a rearward shoulder 92 of the needle shroud tubular portion abutting a forward facing shoulder 94 upstanding from the rear of the tubular portion 36 of the syringe carrier 34. Rearwardly of the barbs 88 on the syringe carrier are two rearwardly facing ramp surfaces 96.

At its rear end, the syringe carrier has four lugs 98 that, when the device is assembled, run in respective slots 100 in the front body portion 20 to limit linear movement of the syringe carrier relative to the front body portion 20. Snap fitted onto the rear of the syringe carrier is the spring guide 46 as shown in FIG. 8 . This has snap fit tabs 102 that snap fit around walls 104 on the rear end of the syringe carrier. The tabs also form a platen surface for the shroud springs 44, with the spring guide fingers 48 passing down the centre thereof. The forward ends of the shroud springs are seated on projecting fingers 106 towards the rear of the arms 30 of the needle shroud 24. About two-thirds of the way back from the front of each slot 90 are two barbs 108 with inclined forward surfaces. Behind each slot 90, on a live hinge is a rearward barb 108, again with an inclined forward surface. The barbs 108 and cooperate 110 with respective opposed barbs 112 about a third of the way down the length of the front body housing 20 on the inner walls thereof.

The arrangement of the barbs in the pre-use position can be clearly seen in FIGS. 14 and 15. In the pre-use position, the barbs 108 on the needle shroud cooperate with the barbs 112 on the front body housing to prevent rearward movement of the needle shroud 24. The forward faces of the barbs 88 on the syringe carrier also cooperate with the barbs 112 on the front body housing on the forward housing to prevent forward movement of the syringe carrier 34 prior to and during removal of the front cap 14. Removing the cap removes a bracing on the barbs which initially prevents inward movement of the barbs so that, when fired, the force of the drive spring causes the barbs 88 to cam past the barbs 112 on the front body housing. During operation of the device, when fired, with the needle shroud 24 held against forward movement by its contact with the skin around the injection site, the sub-assembly of the syringe 13 and the syringe carrier 34 is shifted forwardly, relative to the forward housing to a limit position defined by the lugs 98 reaching the forward ends of the slots 100. After the injection is complete, the needle shroud 24 moves forward as the skin contact pressure is removed from the surface 28 as the device is lifted clear of the skin. This allows the needle shroud to move forwardly under the influence of the shroud springs 46 so that the rear barbs 110 move forwardly and snap past the barbs 112 on the front housing 20 to prevent retraction once the needle shroud has extended. The barbs 110 are braced in this position by the underlying ramp surfaces on the syringe carrier 34.

Referring now to FIGS. 10 and 11, the removable front cap 14 has opposed slots 114 which align with the slots 78 on the rear body housing 56, to frame the window 22 in the front body housing 20 to allow viewing of the dose volume as described above. Referring more particularly to FIG. 11, the cap is elliptical in outer section and has an inner central cylindrical portion 116 extending rearwardly from which extend further two fingers 118 of arcuate cross-section disposed on the major axis of the ellipse. On the inner surface of the fingers, towards the rear ends, are respective inwardly directed barbed ribs 120 with inclined rear surfaces. As seen in FIGS. 14 and 15, the ribs 120 are designed to snap into a gap formed between the forward shoulder on the barrel of the syringe 13 and the rear surface of the rigid needle shield 15 or an aperture therein. When the syringe 13 is loaded into the front assembly 12 (with the cap 14 attached) during manufacture, the rigid needle shroud 15 snaps past the ribs 120 so that they lodge behind the rear edge of the needle shield 15 (or a rear edge of an aperture in the needle shield) as shown. The front cap 14 also has twin shallow scallops 122 which releasably engage pips 124 on the outer surface of the front body housing when the cap is fitted (see FIGS. 14 and 15).

When in the condition as supplied (FIG. 14) the fingers 118 of the cap underlie the spring fingers 86 on the syringe carrier 34 and prevent these from flexing inwardly. In this condition, the fingers 118 thus brace the spring fingers against inward unlatching motion. The forward end of the cylindrical portion 116 of the cap 14 is also provided with inward projections 123 aligned with the minor axis of the ellipse and which prevent forward movement of the rigid needle shield relative to the front cap 14. In this way, when the front cap 14 is withdrawn from the position shown in FIG. 15, the ribs 120 pull the rigid needle shield 15 to ease it off the forward end of the syringe 13. At the same time the presence of the fingers 118 also temporarily locks the syringe carrier 34 (and thus the syringe 13) against forward movement by blocking the fingers 86 against inward movement until the needle shield is off the syringe to prevent the syringe from being pulled forwardly if there is a tight fit between the syringe and the needle shield. When the front cap is free of the device the needle shield 15 is captive in the cap 14, trapped by the ribs 120 and the inward projections 123. Orienting the ribs 120 and the inward projections 123 at 90° means that the open ended cap may be injection-moulded in a simple injection mould with a slide rather than requiring a more complex mould design.

Referring to FIGS. 4, 12 and 15, the firing button 18 is of elliptical form with two split arrowhead tabs 125 aligned with the minor axis, which seat behind respective ribs on the inner rear surface of the rear housing portion 56 to retain the firing button 18 on the rear of the housing and to limit rearward movement thereof. The inner rear surface of the trigger has a firing boss 126 which is of slightly smaller diameter than the outer diameter of the split arrowheads 74 on the rear of the plunger 60 so that, when the firing button 18 is pressed forwardly from the position shown, the boss squeezes the twin arrowheads 74 together to release the barbs 76 from the catchment surface 77 to free the plunger for forward movement. The firing button 18 has an aperture 130 concentric with the boss 126 through which a safety pin 134 on the rear cap 16 passes to hold the split arrowheads apart. Aligned with the major axis of the ellipse are two forwardly extending flexible biasing strips 134 which cooperate with respective bias camming surfaces 136 in the rear end of the rear housing 59, as shown in FIGS. 14(a) and 15(a) to provide a low friction gliding plastic-to-plastic surface contact. The camming surfaces 136 are shaped to provide a predetermined variation of resistance force with distance. The biasing strips cooperate with the curved rear portion of the camming surfaces to provide a bias force tending to restore the button to its rearmost position as defined by the split arrowhead tabs. It is desirable to provide a tactile resistance to movement and to require a few millimetres of movement before the firing boss 126 releases the plunger, to avoid premature firing. A forward portion of the camming surfaces is of shallower inclination and designed to provide a non-reversible resistance to movement after the device has been fired, thereby to trap or wedge the firing button in its forwardmost position. This gives a further useful visual cue to a user as to whether the device has been fired or not. Of course, if required the camming surface may instead be designed to return the button to its original position after firing.

The autoinjector as illustrated includes several safety features to prevent inadvertent firing and to render the device safe after use. It is also highly desirable to resist or prevent disassembly of the device after use. It will be noted from the description and FIG. 2 above that the device is assembled by inserting a syringe into the syringe carrier in the front assembly and then snap-fitting the front and rear assemblies together. The snap fitting is done by means of outwardly facing sprung tabs 138, 140 on the rear of the front body housing 20 which seat simultaneously in respective apertures 142 in the rear body housing 56. One pair of tabs 138 is aligned with the minor axis and one pair 140 with the major axis of the device. It will be appreciated that, given appropriate dexterity and strength, it would be possible to press in all four of the tabs 138, 140 by poking an implement through the recesses 142 from outside and thereby disassemble the device. However, this is prevented in this embodiment by means of two fin formations 144 provided on the plunger 60 as seen in FIGS. 13 and 15(b). The plunger is designed so that, once the device is fired and the plunger is at its post-firing position, the fin formations 144 underlie the tabs 138 on the minor axis of the ellipse, as shown in FIG. 15(b), thereby bracing them against inward deflection and preventing disassembly.

For operation, the user removes the front cap 14 and rear cap 16, thereby arming the device. The device is then offered up to the injection site to press the conical or curved front face of the needle shroud 26 against their skin. When ready, the firing button 18 is pressed, which releases the plunger 60 for forward movement under the action of the main drive spring 58. Initially, due to a sprung engagement finger 145 on the plunger, the plunger and syringe move as one forwardly to extend the needle to penetrate the flesh, with this movement continuing until the lugs 98 on the syringe carrier reach the forward end of the slots 100 on the front body housing, thereby inserting the syringe needle to the required depth. Upon arresting movement of the syringe, the sprung engagement finger 145 flexes inwardly into the bore of the syringe and the plunger continues to move, driving the piston 11 down the syringe body to expel a dose. Alternatively, in other designs of the device, the spring engagement finger may yield so that the plunger starts to move into the syringe before forward movement of the latter is arrested. In either design, when the plunger reaches its forwardmost position, the ball magnet 68 which up till now has been held in the passage 66 on the centre line of the plunger by magnetic attraction to the keeper ball 72 is attracted by the greater force provided by the disc magnet 54 held in the recess of the spring guide, accelerating towards it and impacting the magnet and/or spring guide to produce a loud audible click to indicate to the user that the injection is complete.

The user then removes the device from their skin and the release of pressure on the front end of the needle shroud 24 means that it can now extend forwardly under the influence of the twin shroud springs 44 to move forwardly to shield the needle. As it nears its forwardmost position, the barbs 110 snap past the barbs 112 on the inside of the front housing 20 thereby to prevent retraction of the needle shroud.

The invention claimed is:

1. An autoinjector, comprising:
a front body assembly;
a rear body assembly connected to the front body assembly; and
a removable cap fitted to a forward end of the front body assembly, wherein,
said rear body assembly contains a drive mechanism,
said front body assembly contains a syringe or cartridge with a needle at the forward end thereof,
the front body assembly includes a viewing window through which at least part of the contents of the syringe or cartridge are visible,
the rear body assembly has at least one cut-away region extending rearwardly from a forward end of the rear body assembly,
the removable cap has at least one cut-away region extending forwardly from a rearward end of the removable cap, and
the respective cut-away regions are aligned when the cap is fitted to the forward end of the front body assembly such that the cut-away regions together defining a frame for said viewing window, the frame determining the visible portion of the viewing window when the cap is fitted to the forward end of the front body assembly,
wherein the autoinjector is adapted to receive one of a series of syringes or cartridges of different fill volume, and
wherein an axial extent of at least one of said cut-away regions varies according to the fill volume.

2. The autoinjector according to claim 1, wherein the axial extent of the cut-away region in the rear body assembly is variable.

3. The autoinjector according to claim 2, wherein said drive mechanism includes a plunger of length selected dependent on the fill volume.

4. The autoinjector according to claim 1, wherein said drive mechanism includes a plunger of length selected dependent on the fill volume.

5. The autoinjector according to claim 1, wherein said drive mechanism includes a plunger of length selected dependent on the fill volume.

6. The autoinjector as claimed in claim 1, wherein the frame defined by the cut-away region of the rear body assembly and the removable cap substantially surrounds the viewing window when the cap is fitted to the forward end of the front body assembly.

7. The autoinjector as claimed in claim 1, wherein the at least one cut-away region of the rear body assembly and the at least one cut-away region of the removable cap are substantially aligned in the axial direction of the autoinjector.

8. A method of manufacturing one of a range of autoinjectors having syringes or cartridges with different preset fill volumes, which method comprises:
providing a front body assembly,
inserting one of a series of syringes or cartridges of different fill volume into a forward end of said front body assembly,
providing a rear body assembly which includes a rear body housing containing a drive mechanism comprising a drive plunger, the length of the drive plunger having been selected from a range of plungers of different length according to the fill volume of the syringe or cartridge,
assembling said autoinjector by connecting together said front and rear body assemblies, and
providing a removable cap fitted to the forward end of the front body assembly, wherein,
the front body assembly includes a viewing window through which at least part of the contents of the syringe or cartridge are visible,
the rear body assembly has at least one cut-away region extending rearwardly from a forward end of the rear body assembly,
the removable cap has at least one cut-away region extending forwardly from a rearward end of the removable cap, and
the respective cut-away regions are aligned when the cap is fitted to the forward end of the front body assembly such that the cut-away regions together defining a frame for said viewing window, the frame determining the visible portion of the viewing window when the cap is fitted to the forward end of the front body assembly, and wherein an axial extent of at least one of said cut-away regions varies according to the fill volume.

9. A method according to claim 8, wherein the front body assembly is of common design for each of the range of autoinjectors.

* * * * *